United States Patent
Reimels

(10) Patent No.: US 9,681,905 B2
(45) Date of Patent: Jun. 20, 2017

(54) EXPANDABLE SCREW AND METHODS OF USE

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 378 days.

(21) Appl. No.: 14/039,520

(22) Filed: Sep. 27, 2013

(65) Prior Publication Data

US 2014/0094860 A1    Apr. 3, 2014

Related U.S. Application Data

(60) Provisional application No. 61/708,884, filed on Oct. 2, 2012.

(51) Int. Cl.
| | |
|---|---|
| *A61B 17/84* | (2006.01) |
| *A61B 17/86* | (2006.01) |
| *A61B 17/88* | (2006.01) |
| *A61B 17/70* | (2006.01) |

(52) U.S. Cl.
CPC ........ *A61B 17/844* (2013.01); *A61B 17/8625* (2013.01); *A61B 17/8635* (2013.01); *A61B 17/8685* (2013.01); *A61B 17/7037* (2013.01); *A61B 17/864* (2013.01); *A61B 17/8875* (2013.01); *A61B 2017/8655* (2013.01)

(58) Field of Classification Search
CPC ......................................... A61B 17/84–17/869
See application file for complete search history.

(56) References Cited

U.S. PATENT DOCUMENTS

| | | | | |
|---|---|---|---|---|
| 1,278,025 | A * | 9/1918 | Salmons | F16B 13/065 411/32 |
| 5,702,216 | A * | 12/1997 | Wu | F16B 13/066 411/32 |
| 7,491,236 | B2 * | 2/2009 | Cragg | A61B 17/70 606/301 |

(Continued)

FOREIGN PATENT DOCUMENTS

| | | |
|---|---|---|
| DE | 29615691 U1 | 10/1996 |
| WO | 2012142538 A1 | 10/2012 |

OTHER PUBLICATIONS

Extended European Search Report for EU13763PTEP-Dz dated Jun. 10, 2016.

*Primary Examiner* — Zade Coley
(74) *Attorney, Agent, or Firm* — Dinsmore & Shohl LLP

(57) ABSTRACT

An expandable screw includes generally a shaft, a head, and a cut pattern. The shaft includes a longitudinal axis, an outer surface including a thread to engage bone, and an expandable region configurable between a first state with a first radius measured from the longitudinal axis to the outer surface and a second state having a second radius measured from the longitudinal axis to the outer surface. The head coupled with the shaft at a neck is configured to receive a driving instrument to insert and drive the shaft into the bone when the expandable region is in the first state. The cut pattern on the shaft permits at least partial nesting of a first portion of the expandable region within a second portion of the expandable region in the second state.

20 Claims, 14 Drawing Sheets

(56) References Cited

U.S. PATENT DOCUMENTS

| | | | |
|---|---|---|---|
| 8,388,660 B1* | 3/2013 | Abdou | A61B 17/8685 606/267 |
| 8,636,784 B2* | 1/2014 | Greenhalgh | A61B 17/864 606/313 |
| 9,072,561 B2* | 7/2015 | Jacofsky | A61B 17/686 |
| 9,155,578 B2* | 10/2015 | Chegini | A61B 17/844 |
| 2005/0113928 A1* | 5/2005 | Cragg | A61B 17/70 623/17.16 |
| 2009/0125071 A1* | 5/2009 | Skinlo | A61B 17/0401 606/300 |
| 2009/0131992 A1* | 5/2009 | Greenhalgh | A61B 17/864 606/313 |
| 2009/0204216 A1 | 8/2009 | Biedermann et al. | |
| 2009/0248089 A1* | 10/2009 | Jacofsky | A61B 17/686 606/311 |
| 2010/0234904 A1 | 9/2010 | Richelsoph | |
| 2011/0144703 A1* | 6/2011 | Krause | A61B 17/8625 606/309 |
| 2011/0319946 A1* | 12/2011 | Levy | A61B 17/7035 606/309 |
| 2012/0109222 A1* | 5/2012 | Goel | A61B 17/8625 606/310 |
| 2012/0184993 A1* | 7/2012 | Arambula | A61B 17/7064 606/246 |

\* cited by examiner

EXPANDABLE SCREW AND METHODS OF USE

CROSS-REFERENCE TO RELATED APPLICATIONS

The present application claims priority to U.S. Provisional Application Ser. No. 61/708,884 entitled "Expanding Screw Apparatus and Methods of Use" which was filed on Oct. 2, 2012 and is incorporated herein by reference in its entirety.

FIELD

The present disclosure generally relates to spinal orthopedic, and more particularly to devices and methods for expanding and removing expandable screws from bone.

BACKGROUND

The spine is a flexible column formed of a plurality of bones called vertebrae. The vertebrae are hollow and stack one upon the other, forming a strong hollow column for support of the cranium and trunk. The hollow core of the spine houses and protects the nerves of the spinal cord. The different vertebrae are connected to one another by means of articular processes, ligaments, and intervertebral, fibrocartilaginous bodies known as disks. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae. The spine is held upright through the work of the back muscles, which are attached to the vertebrae.

The spinal disks act as shock absorbers, cushioning the spine, and preventing individual bones from contacting each other. Disks also help to hold the vertebrae together. The weight of the upper body is transferred through the spine to the hips and the legs. Disks may degenerate, herniated, bulge, or burst and impinge on the nerves between the vertebrae causing pain.

While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature. Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior, lateral, and posterior approaches and others in between.

Certain spinal conditions, including a fracture of a vertebra and a herniated disc, indicate treatment by spinal immobilization. Several systems of spinal joint immobilization are known, including surgical fusion and the attachment of pins and bone plates to the affected vertebras. Known systems include screws having proximal heads and threaded shafts that may be inserted into at least two spaced-apart vertebras. The screws may receive fixation rods to stabilize the spine during fusion.

Some screws may be expandable in order to enhance stability within the vertebra, for example when the vertebra suffers from degeneration, osteoporosis, and other conditions that cause the bone to become brittle. These expandable bone screws may allow bone ingrowth through expanded cells of the screw. In some instances such as revision surgeries, it may be necessary to remove the expanded screw. However, once the bone becomes mineralized, it reduces the ability of the expanded cells to collapse back to the base diameter of the screw.

SUMMARY

Provided herein are devices and methods for preventing bone ingrowth inside an expandable screw. An expandable screw includes generally a shaft, a head, and a cut pattern. The shaft includes a longitudinal axis, an outer surface including a thread to engage bone, and an expandable region configurable between a first state with a first radius measured from the longitudinal axis to the outer surface and a second state having a second radius measured from the longitudinal axis to the outer surface. The head coupled with the shaft at a neck is configured to receive a driving instrument to insert and drive the shaft into the bone when the expandable region is in the first state. The cut pattern on the shaft permits at least partial nesting of a first portion of the expandable region within a second portion of the expandable region in the second state.

In other features, the first portion forces the second portion radially outward as the first portion nests within the second portion. In still other features, the cut pattern forms a first cut surface and a second cut surface, the first cut surface substantially engaged with the second cut surface in the first state. In still other features, the cut pattern forms a first cut surface and a second cut surface, the first cut surface at least partially advanced along the longitudinal axis past the second cut surface in the second state. In yet other features, the cut pattern forms a cut angle measured from the longitudinal axis and in a plane intersecting the longitudinal axis, the cut angle including a non-normal angle.

In other features, the cut pattern forms a first cut surface on the first portion and a second cut surface on the second portion, wherein the second cut surface is disposed opposite the first cut surface in the first state and engages a depth of the thread on the first portion in the second state. In still other features, the cut pattern forms a first cut surface on the first portion and a second cut surface on the second portion, wherein the second cut surface is disposed opposite the first cut surface in the first state and opposite a portion of the thread on the first portion the second state. In yet other features, the cut pattern includes a spiral cut substantially parallel with a spiral path of the thread.

In other features, the expandable region includes a hollow length of the shaft having a sidewall, a first section of the sidewall at least partially overlapping a second section of the side wall in the second state. In still other features, the expandable region includes a hollow length of the shaft formed by a circumferential sidewall and the cut pattern traverses a thickness of the sidewall.

In other features, the expandable screw includes a center post extending distally from the head less than a length of the shaft, coaxial with and internal to the shaft to provide support to the shaft, and including a central lumen for receiving a deployment instrument.

An expandable screw includes a screw, a threaded surface, and a cut pattern. The screw includes a proximal portion, a distal portion, a longitudinal axis, and a shaft portion, wherein the shaft portion is substantially coaxial with the longitudinal axis. The threaded surface includes at least one thread disposed on the shaft portion. The cut pattern traverses the thickness of the shaft portion as to form a plurality of threaded portions, whereby the threaded portions coaxially expand at least a portion of the shaft portion along the longitudinal axis to an expanded state, whereby adjacent threaded portions nest against each other to maintain a closed structure.

In other features, the plurality of threaded portions includes at least one threaded portion that expands coaxially greater than an adjacent threaded portion in the expanded state. In still other features the plurality of threaded portions includes a top portion and a bottom portion, whereby the top portion of one threaded portion abuts against the bottom portion of an adjacent threaded portion in the expanded state.

In other features, the top portion includes an angled inner surface that abuts with the bottom portion of an adjacent threaded portion, as to maintain the closed structure. In still other features, the cut pattern is substantially parallel to the threaded surface.

In other features, the expandable screw includes a head portion coupled to a neck portion disposed substantially within the proximal portion of the screw and the head portion coupled to a center post coaxially disposed within the shaft portion, whereby the application of force to the head portion coaxially expands the threaded portions of the shaft portion.

A method for expanding a screw includes the steps of coaxially engaging a shaft portion of a screw through a center post, disposing at least one thread on the surface of the shaft portion, imparting a cut pattern traversing the thickness of the shaft portion as to form a plurality of threaded portions, coaxially expanding the plurality of threaded portions along at least a portion of the shaft portion along to an expanded state of the screw, and nesting adjacent threaded portions against each other to maintain a closed structure in the expanded state.

In other features, the method includes the step of coaxially expanding at least one threaded portion greater than an adjacent threaded portion. In still other features, the method includes the step of nesting a top portion of the threaded portion with a bottom portion of an adjacent threaded portion in the expanded state.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1A:
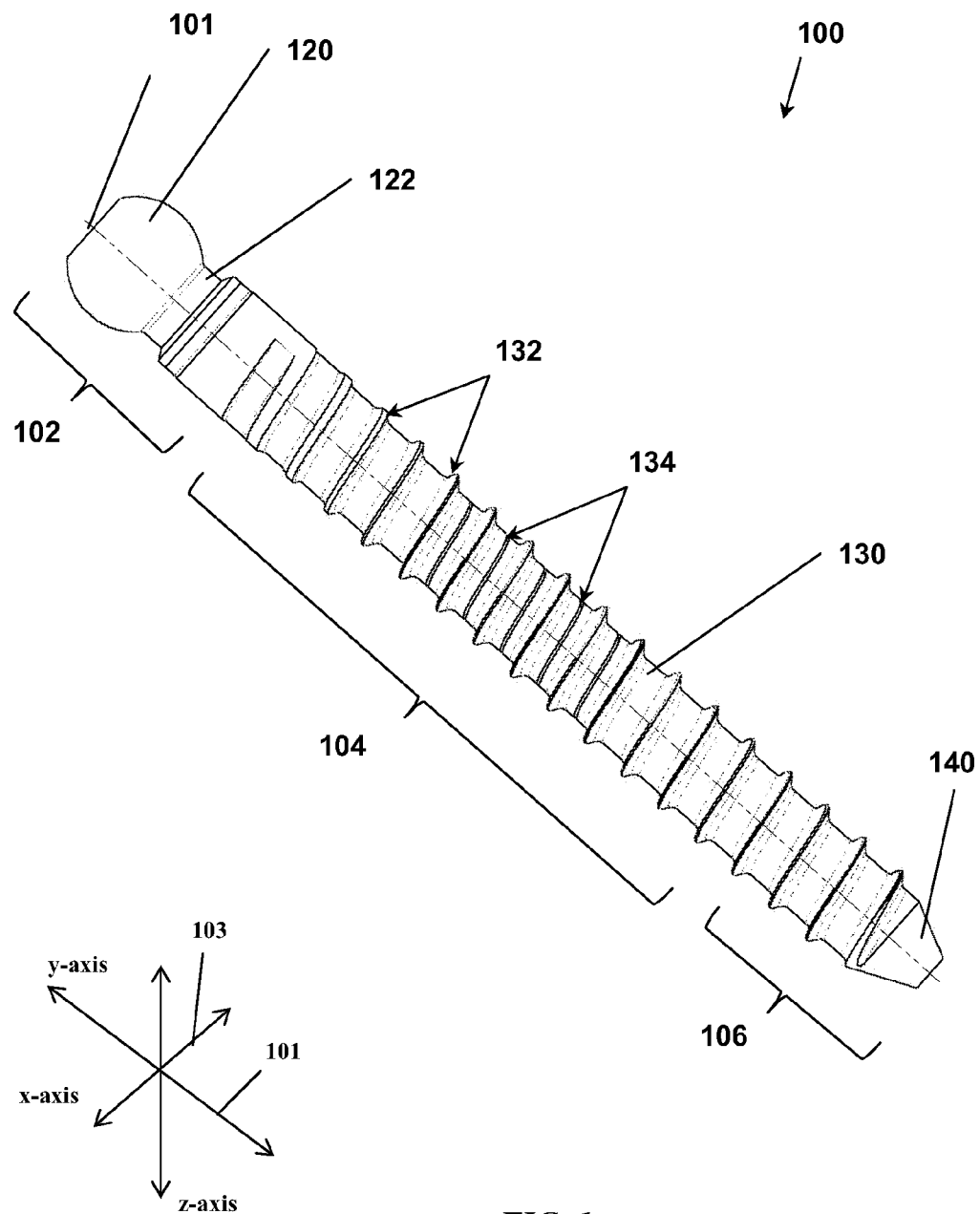
FIG. 1A is a perspective view of one embodiment of the expanding screw.

With reference to FIG. 1a, the expanding screw 100 comprises a proximal portion 102, a distal portion 106, and a middle portion 104 therebetween. The longitudinal axis 101 of the expanding screw 100 is generally shown in the y-axis direction, while the transverse axis 103 is generally shown in the x-axis direction. The proximal portion 102 includes a head portion 120 coupled to a neck portion 122, and a shaft portion 130 traversing the middle portion 104. The distal portion 106 may include a conical tip 140.

Figure 2:
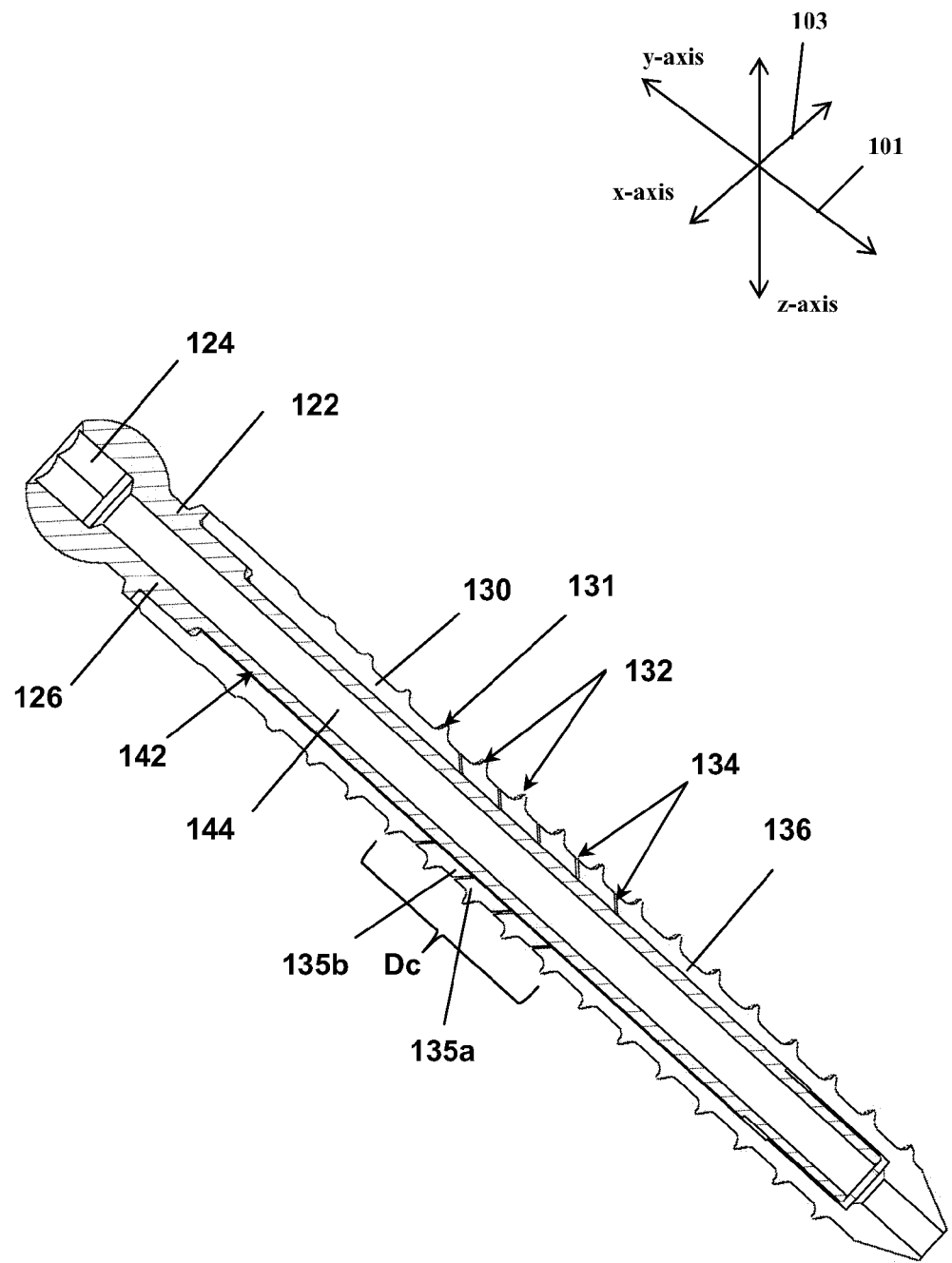
FIG. 2 is a cross-section view of one embodiment of the expanding screw.

In some examples (not shown), the screw further includes other components such as those described in U.S. Publication No. 2008/0243189 and U.S. Pat. No. 7,377,923 referenced above. The expanding screw 100 may comprise a substantially spherical head portion 120; alternatively, the head portion 120 may be polygonal-shaped and the like. As shown in FIG. 2, the head portion 120 further includes a tool engagement recess 124 defined by the head portion 120 for use in driving the pedicle screw into vertebrae or bone. The expanding screw 100 may be used in connection with fixed, mono-axial, or polyaxial screw assemblies and the like.

Figure 1B:
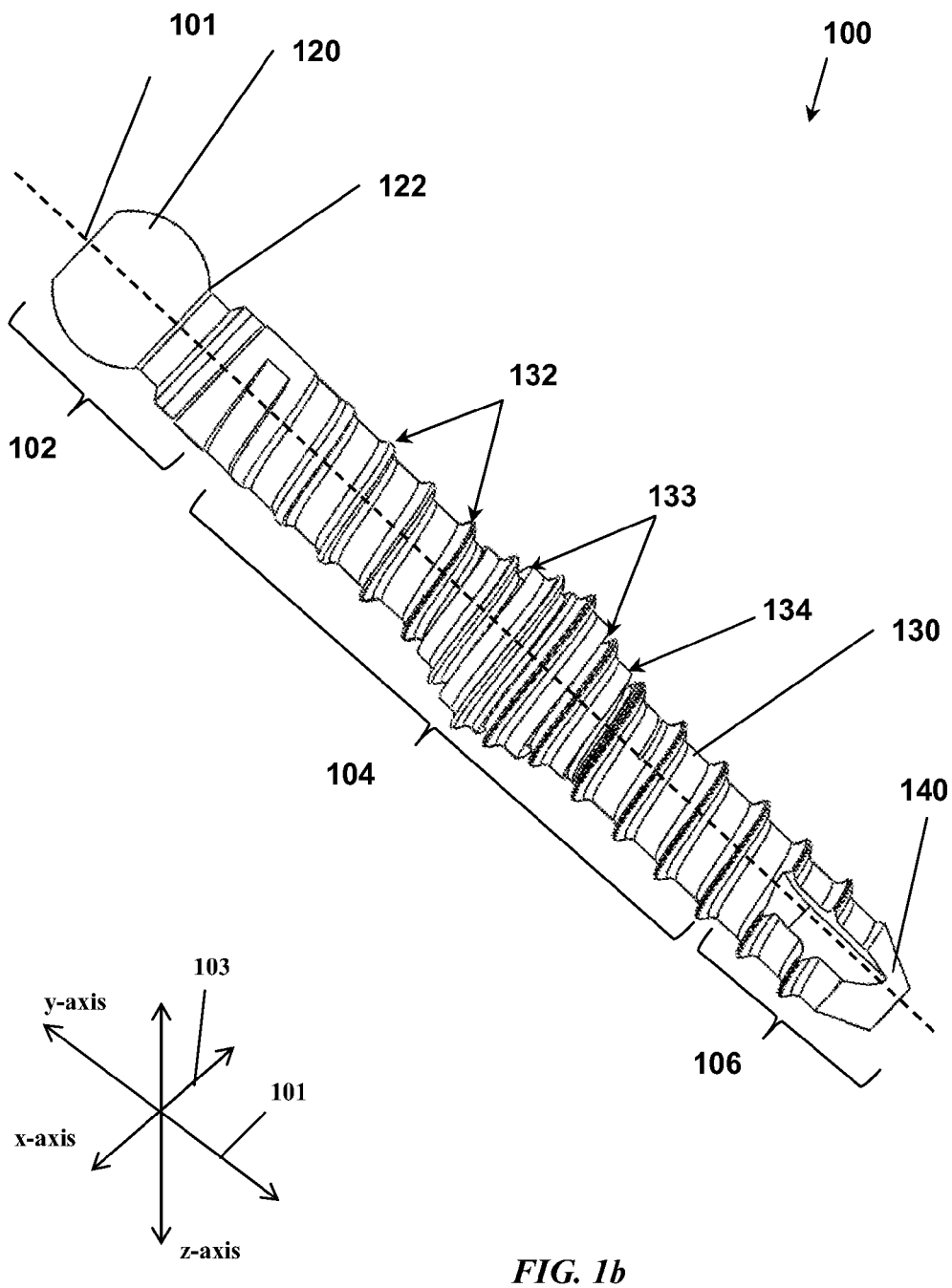
FIG. 1B is a perspective view of one embodiment of the expanding screw in the expanded state.

The shaft portion 130 includes a threaded surface 132 on the exterior of the shaft portion 130, wherein the threaded surface includes at least one thread 131 extending beyond the exterior of the shaft portion. The shaft portion 130 includes a cut pattern 134 that traverses the exterior surface 132 of the shaft portion 130, as shown in FIG. 2. The cut pattern 134 will prevent bone ingrowth inside the expanded implant when the expanding screw 100 is in the expanded state, as shown in FIG. 1b. In one example, the cut pattern 134 is laser cut. Lasers that may be used to dispose the cut patterns include pulse lasers such as femto-second lasers and continuous wave lasers. In other examples, the cut pattern 134 is mechanically cut with a cutting tool.

Those having skill in the art are necessarily familiar with lasers and cutting tools having the capability to dispose cuts onto metal surfaces. Laser machining methods, including by way of example and not limitation, using a femto-second laser, using an excimer laser, using a Laser MicroJet (water assisted), laser assisted chemical machining, fiber laser chirped pulsed amplifiers, or other laser combinations. Photolithographic methods coupled with chemical, electrochemical, reactive ion etch (RIE) micro-machining techniques, may be employed in-lieu of a laser machining method to machine stent pattern designs when appropriate.

In other examples, the exterior surface 132 is patterned by a laser machining process or method employing a femto-second laser to create micron-sized structures without linear optical absorption of the material that can often lead to heat deposition, micro-cracks, and small collateral damage to the surrounding area. Laser assisted chemical machining may also include non-laser forms of light sources, such as super-luminescent diodes (SLD), and the like. This technique can be described as photo-catalytic or photo-activated chemical machining using, for example, UV light as the catalyst to activate/initiate chemical reaction in exposed areas.

In other examples, the cut pattern 134 is created through a mold. While not intending to be bound by any theory of action, the screw may be manufactured by casting material in or on a mold designed to dispose a cut pattern 134 on the shaft portion 130 of the expanding screw 100. The mold may leave a thin residual layer of material to form the cut pattern 134. Alternatively, the thin layer may comprise another material layered onto the screw. The thin layer of material remains either on an exterior portion of the cut pattern 134, or an interior portion of the cut pattern 134 and may break as mechanical stress is applied to the thin layer as the expanding screw 100 is screwed into the bone or expanded. In another example, the expanding screw 100 may be manufactured such that the expanding screw 100 may require winding. While not intending to be bound by any theory of action, the portion of the screw wherein the cut pattern 134 extends may resemble a thin ribbon-like portion of an unwound spring wherein the edges are cut, molded, or filed to a specific angle. The thin metal portion is wound in a spiral fashion such that the edges intimately contact the corresponding side.

As shown in FIG. 2, the neck portion 122 and the head portion 120 may be coaxially coupled to a center post portion 142 that coaxially traverses the center shaft 130. The center post portion 142 may include a central lumen 144. The neck portion 122 may include a lip 126 to longitudinally compress the center shaft 130 to open the cut pattern 134 to the expanded state. For example, a deployment device or tool engages with the engagement recess 124 and pushes down or distally on the center shaft 130 by way of the lip 126. The tool may include a deployment rod that extends through the center post portion 142 and the central lumen 144 to couple with a distal end of the shaft portion 130, such as the conical tip 140. The compressive force on the center shaft 130 forces the cut pattern 134 to open and spiral coaxially outward along the longitudinal axis 101 to an expanded state of the expanding screw 100, while simultaneously allowing adjacent threaded portions 133 to nest against each other maintaining a closed structure or fluid seal as to prevent bone ingrowth inside the expanding screw 100.

Figure 1C:
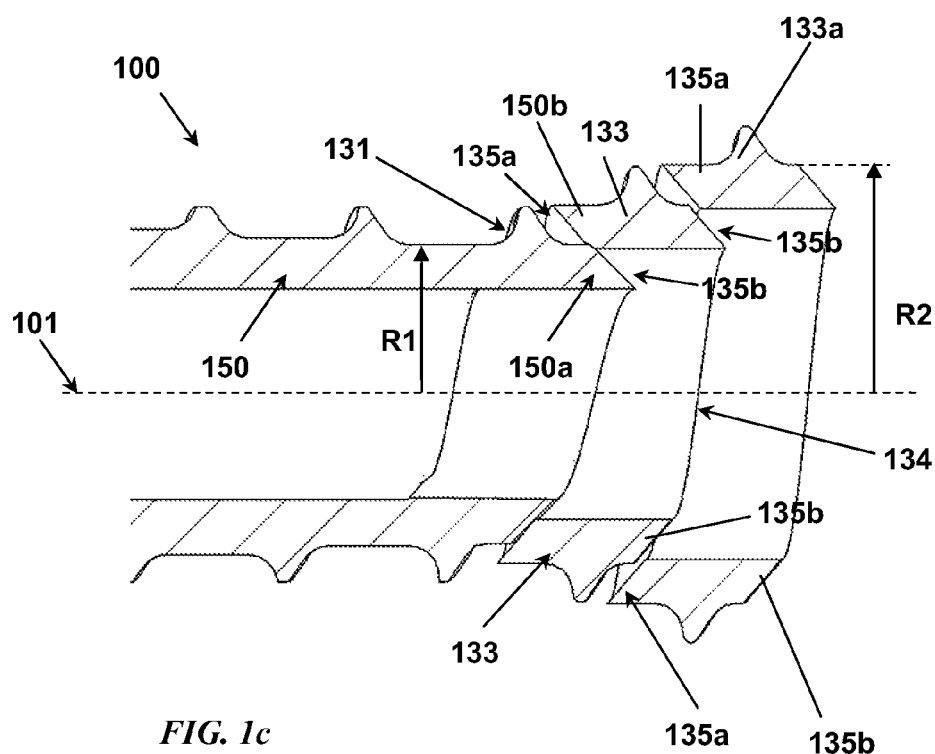
FIG. 1C is a cross-sectional side view of the expanding screw in the expanded state.
Figure 1D:
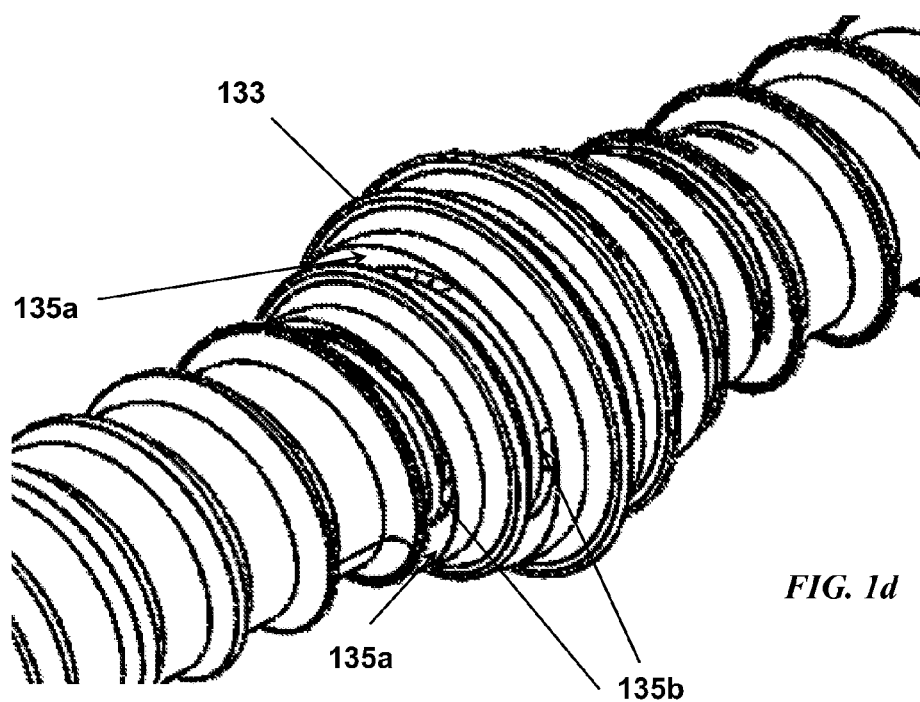
FIG. 1D is an enlarged perspective view of the expanding screw in the expanded state.

The center post portion 142 may be shorter in length than the outer shaft 130. In one embodiment, the tip of the center post 142 has a hex nut pattern that engages with a mating feature near the distal end of the outer shaft 130. In the unexpanded state, the least constrained threaded portion 133a coupled with the cut pattern 134 may expand coaxially first or coaxially expand greater than other threaded portions 133, as the threaded portions 133 radially expand upon application of force. As shown in FIG. 1c, each threaded portion 133 in the expanded state includes a top portion 135a and a bottom portion 135b, whereby the top portion 135a of one threaded portion 133 abuts or nests against the bottom portion 135b of an adjacent threaded portion 133. As shown in FIGS. 1c-1d, the top portion 135a includes the angled inner cut surface that abuts or nests with the bottom portion 135b, as to form a closed expanded structure.

Figure 2A:
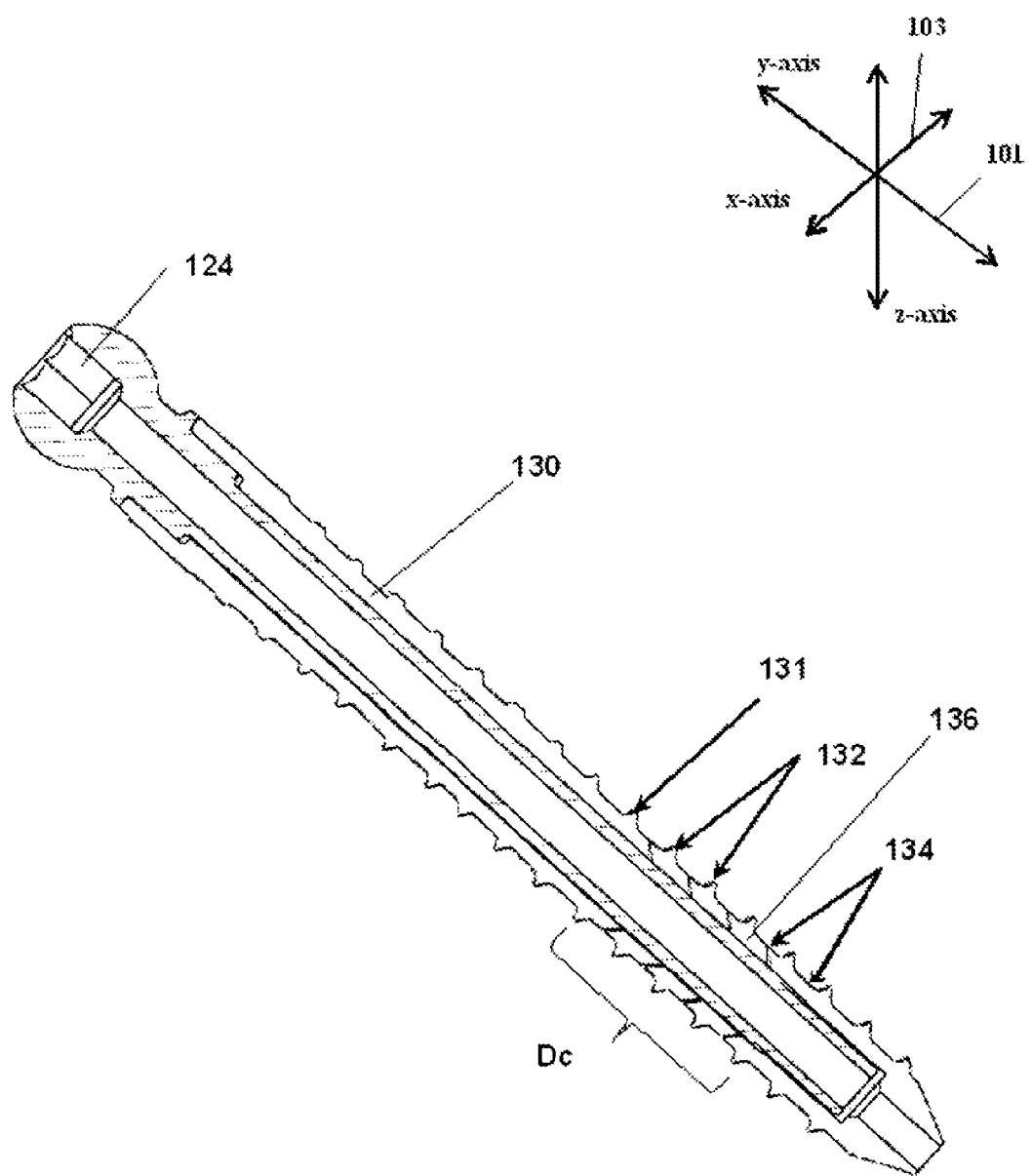
FIG. 2A is a cross-section view of one embodiment of the expanding screw wherein the cut pattern is disposed at the distal portion of the expanding screw.
Figure 2B:
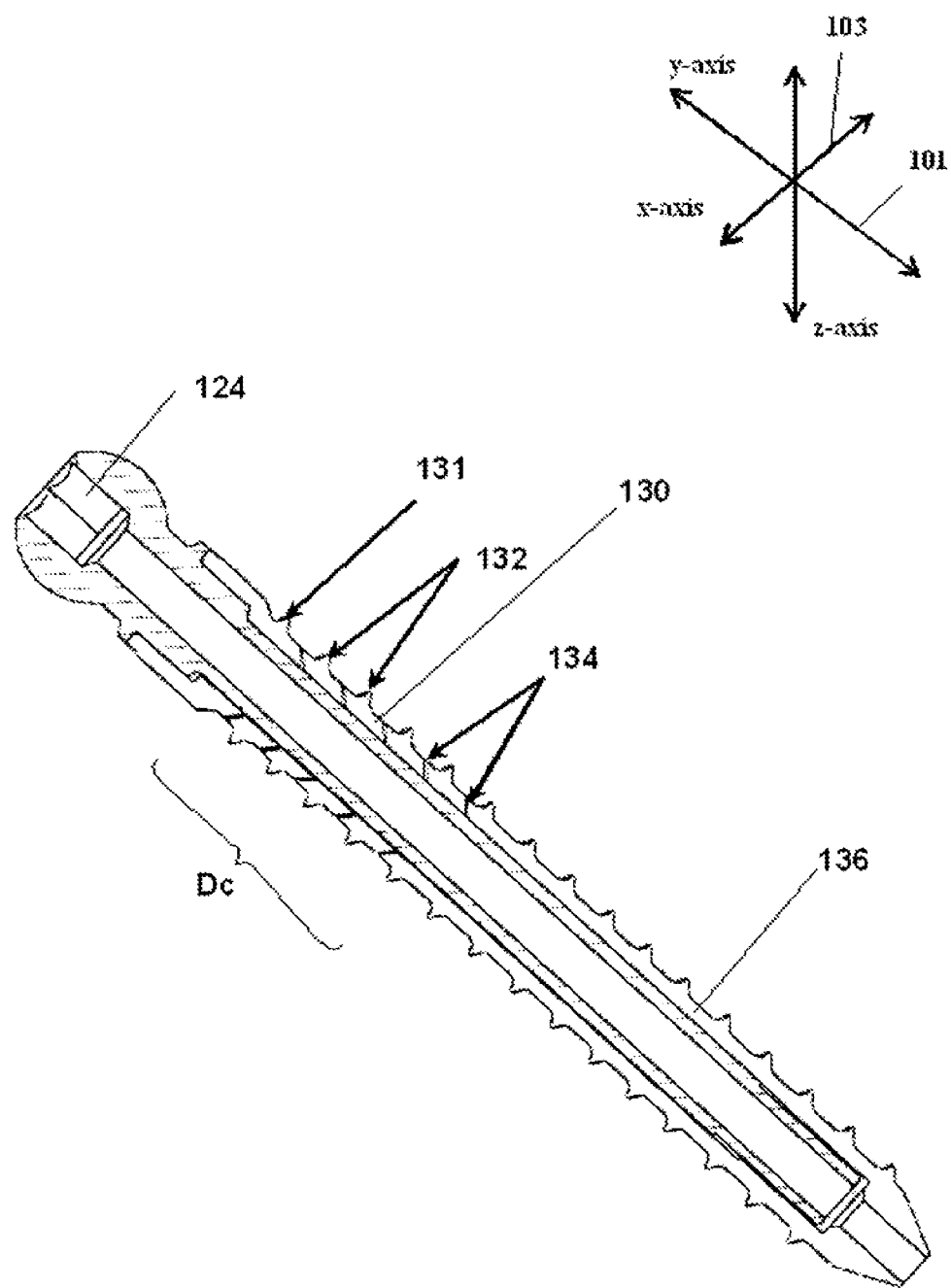
FIG. 2B is a cross-section view of one embodiment of the expanding screw wherein the cut pattern is disposed at the proximal portion of the expanding screw.
Figure 2C:
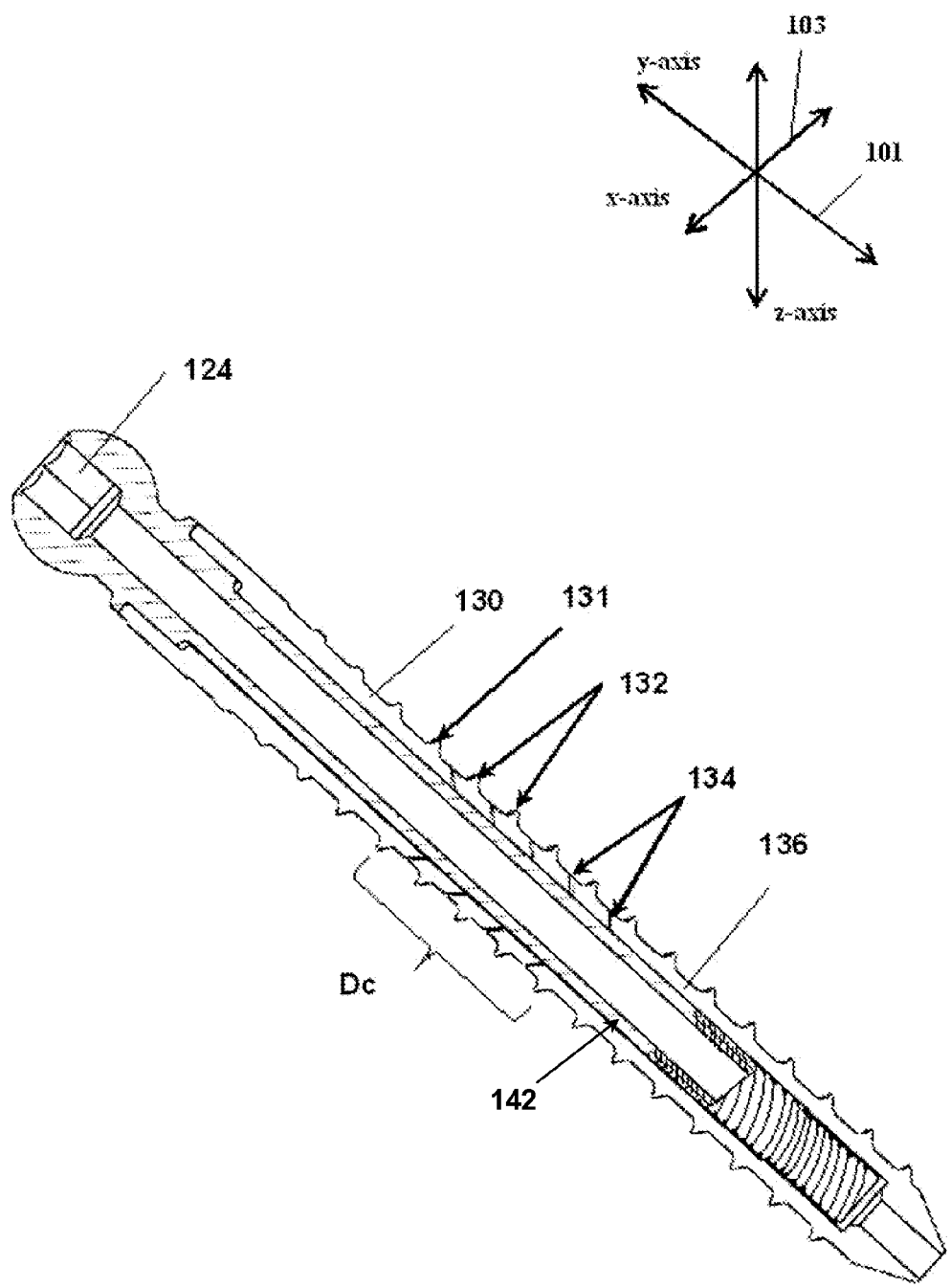
FIG. 2C is a cross-section view of one embodiment of the expanding screw.

In one embodiment as shown in FIG. 2, the cut pattern 134 extends along the middle portion 104 of the shaft portion for a distance of Dc. The cut pattern 134 extends along the base or root of the thread 131 and consequently, includes a spiral pattern along the circumference of the exterior surface of the shaft portion. Preferably, the cut pattern 134 mirrors the spiral pattern of the threaded surface 132, such that the cut pattern 134 is symmetrical or parallel with the threaded surface 132. Alternatively, the cut pattern 134 may be asymmetrical or transverse with the threaded surface 132. In another embodiment as shown in FIG. 2a, the cut pattern 134 extends along the distal portion of the shaft portion 142 for a distance of Dc. In yet another embodiment as shown in FIG. 2b, the cut pattern 134 extends along the proximal portion of the shaft portion 142 for a distance of Dc. As shown in FIG. 2c, the center post portion 142 of the expandable screw may include a shortened portion of the distal end, which allows the distal movement of the center post portion 142.

Figure 3:
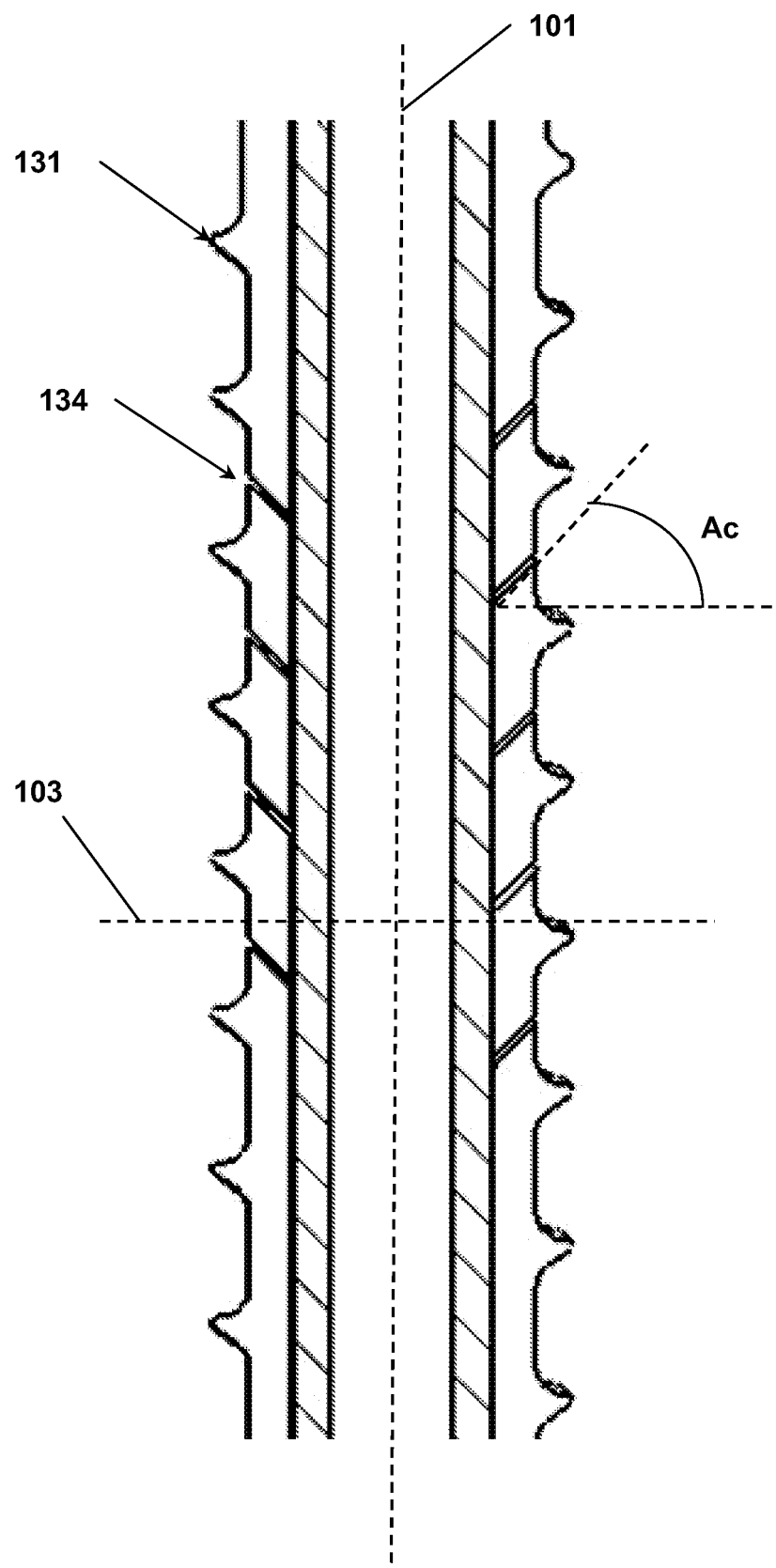
FIG. 3 is an enlarged cross-sectional view of one embodiment of the expanding screw.

As shown in FIG. 3, the angle of the cut pattern 134 includes an angle Ac that is not normal to the longitudinal axis 101 of the expanding screw 100, which permits the top portion 135a to nest or abut with the bottom portion 135b in the expanded state of the expanding screw 100. In one embodiment, the angle Ac is about 45° relative to the longitudinal axis 101 or transverse axis 103; alternatively the angle Ac is about 135° relative to the longitudinal axis 101 or transverse axis 103; alternatively the angle Ac may be between about 0° and 180°; alternatively, angle Ac may be between about 25° and 150°; alternatively, the angle Ac may be between about 35° and 125°; alternatively, the angle Ac may be between about 40° and 100°; alternatively the angle Ac may be between 45° and 85°; and alternatively the angle Ac may be between 135° and 175°. Alternatively, the angle Ac may be adjusted to vary the amount of expansion of the expanding screw, such that greater angles Ac allow for greater radial expansion along the longitudinal axis for the top portion 135a and the bottom portion 135b to nest and form an expanded closed structure.

Figure 4:
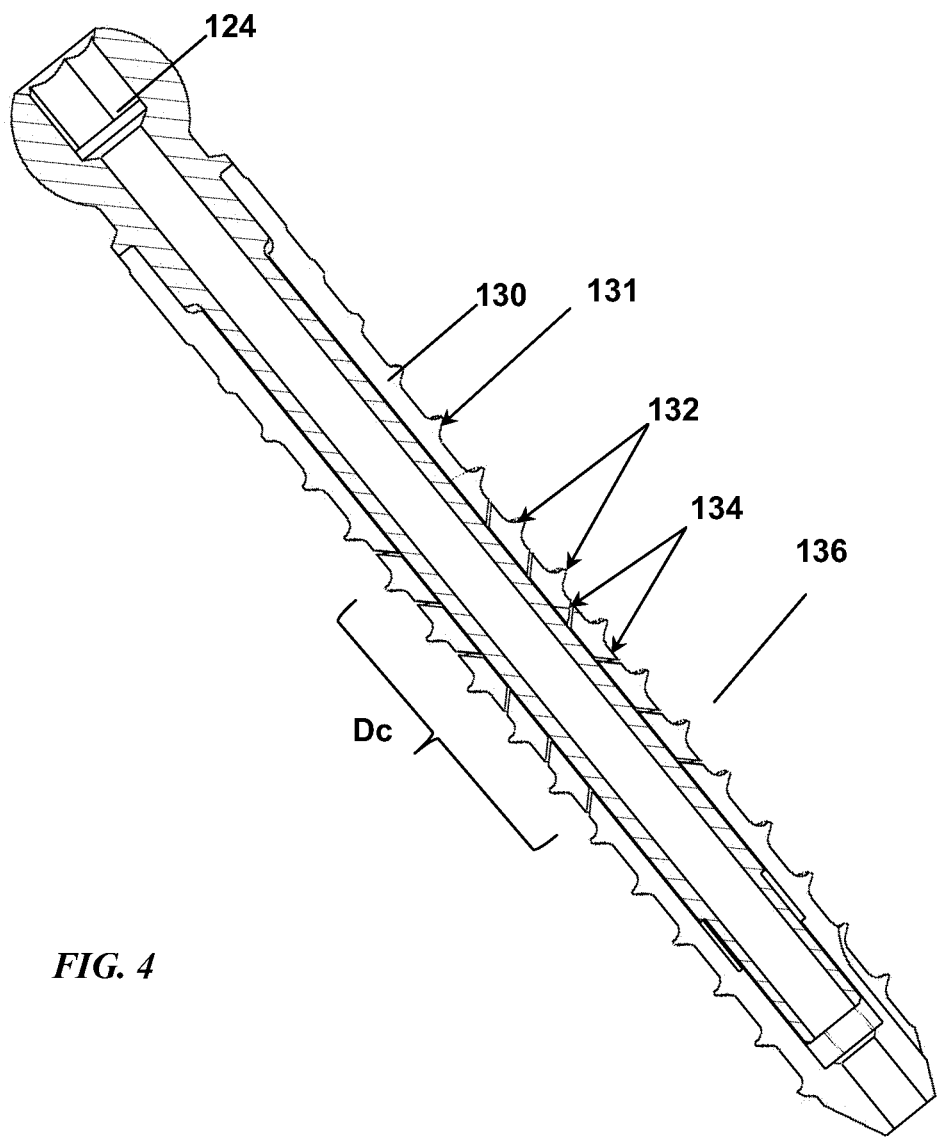
FIG. 4 is a cross-sectional view of one embodiment of the expanding screw.
Figure 5:
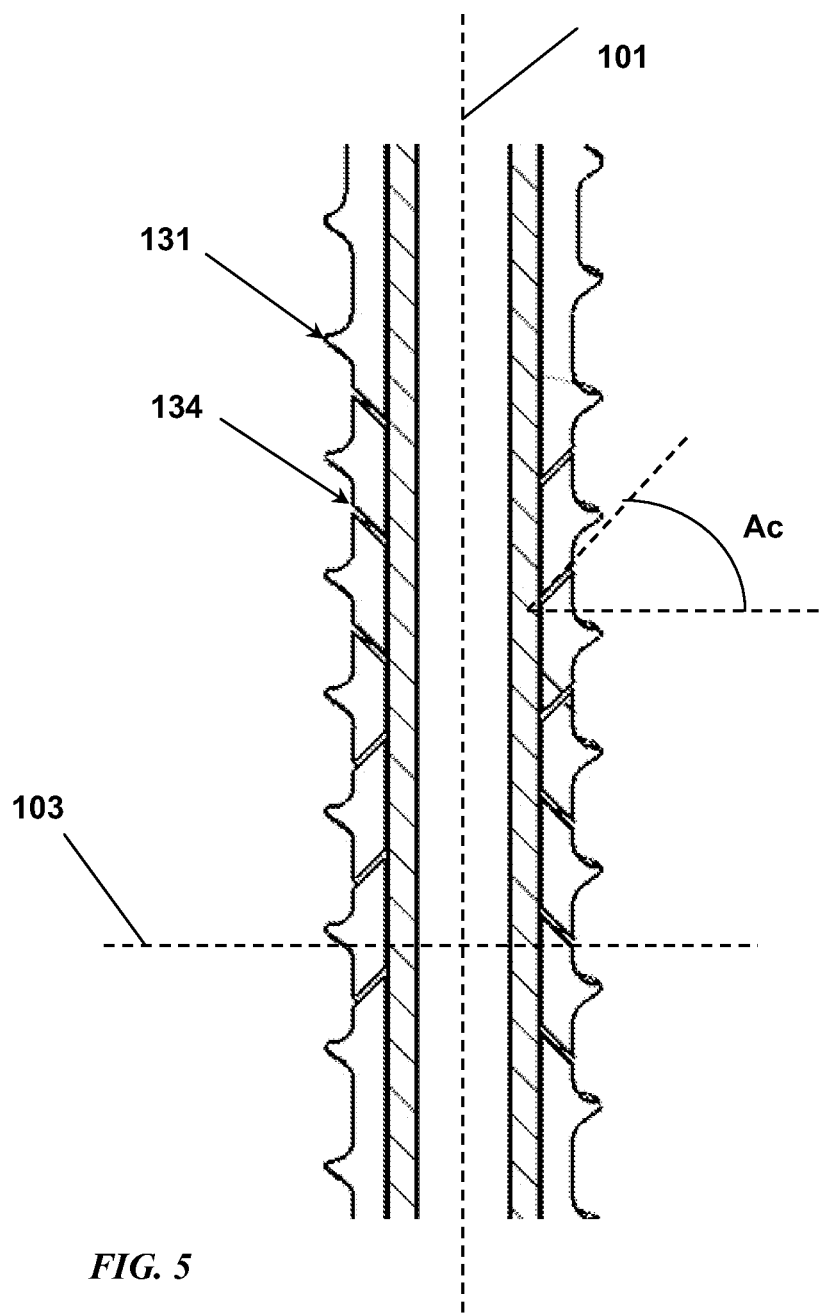
FIG. 5 is an enlarged cross-sectional view of the embodiment in FIG. 4.

The angle Ac of the cut pattern 134 will result in a profile wherein the threaded surface 132 radially expands relative to the longitudinal axis 101 when the expanding screw 100 expands to the expanded state, which causes an upper thread 131 to be driven below an adjacent thread 131. When the expanding screw is in the expanded state, the expanded profile will be compressed and force adjoining slit threads to nest together forcing the lower threads to expand outward as the upper threads tunnel under each lower adjacent thread. The thread nesting will cause the expanded threads to form a profile. The angle Ac of the cut pattern could vary along the path of the slit or be reversed at the midpoint to ensure uniform thread expansion, as shown in FIG. 4.

Figure 11A:
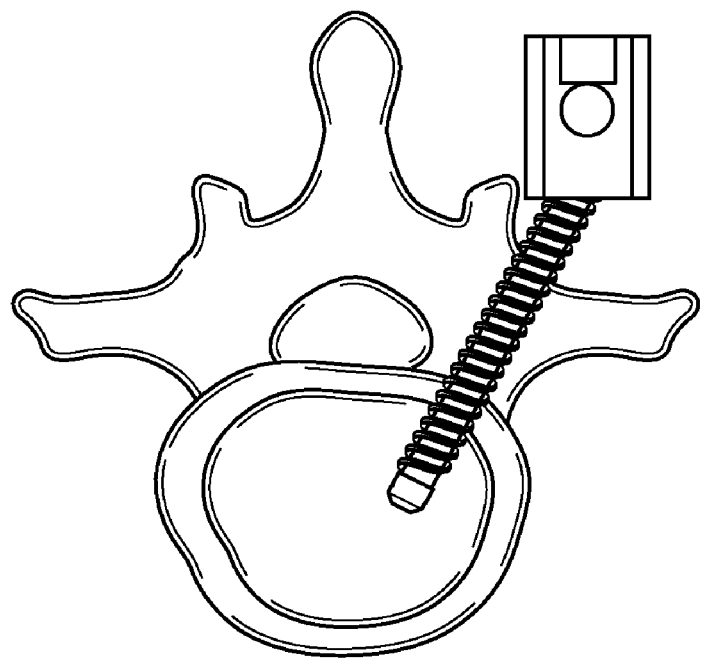
FIG. 11A is a top view showing the expandable screw normally attached to the posterior side of a healthy vertebra through the pedicle of the vertebra using a polyaxial pedicle screw with a housing to connect the head of the screw to a rod of the spinal fixation system.
Figure 11B:
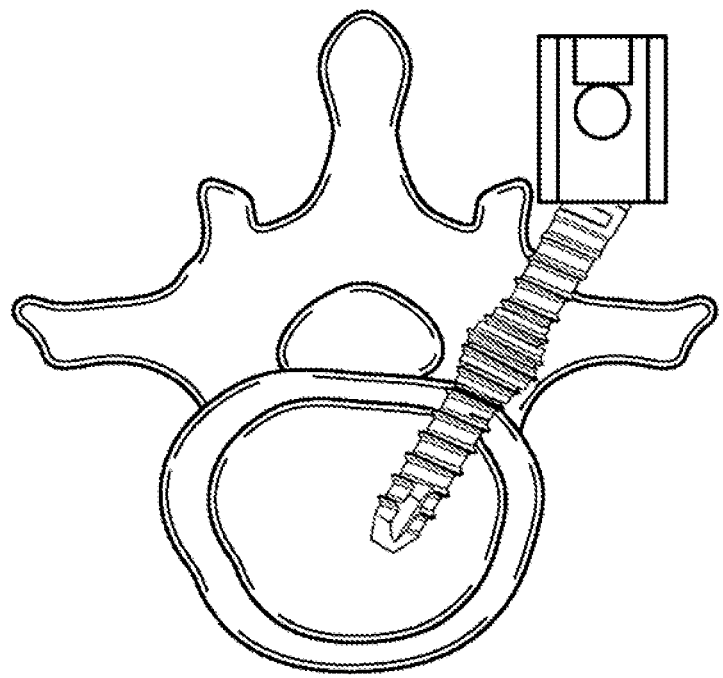
FIG. 11B is a top view showing the expandable screw in the expanded state attached to the posterior side of a healthy vertebra through the pedicle of the vertebra.

As shown in FIGS. 1B, 1D, and 11B, since each thread overlaps the adjacent thread in the expanded area of the implant there is no pathway for bone to penetrate inside the screw. The resulting nested interlocked threads of the screw expansion area will stack together to form a stable construct. The thread profile or pitch of the screw may also need to be modified to optimize the screw expansion. In order to preserve pullout force of the existing expanding screws, a lock may be used to maintain the screw in the deformed expanded state. This lock may take the form of a snap between the distal and proximal parts of the expanding screw. The lock may be a center strut, ratchet type mechanism, screw, locking arm, combinations thereof that can be integral with or separate from the remainder of the expandable screw 100.

The center post 142 of the screw 100 may provide structure of the screw and will provide a base to ensure expansion in a radially outward direction. The center post 142 may comprise a threaded distal end and a length such that resistance at the distal portion 106 causes the center post 142 to rotate as the head portion 120 is actuated by an engagement tool. A lower deployment force may allow the development of smaller diameter screws since the deployment shaft diameter could be decreased proportionally. An optional deployment tool may be a method and device for implant deployment as described in commonly owned U.S. Publication No. 2009/0318928, incorporated by reference herein.

Figure 6A:
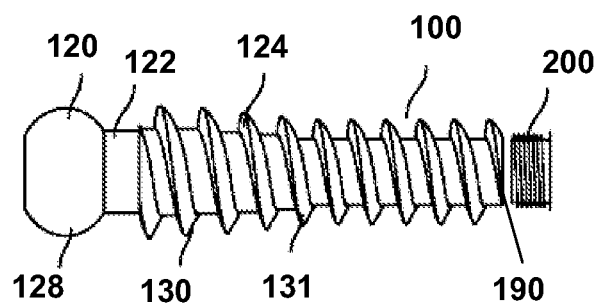
FIG. 6A is a side view of the expandable screw with an attachment point on the distal section.
Figure 6B:
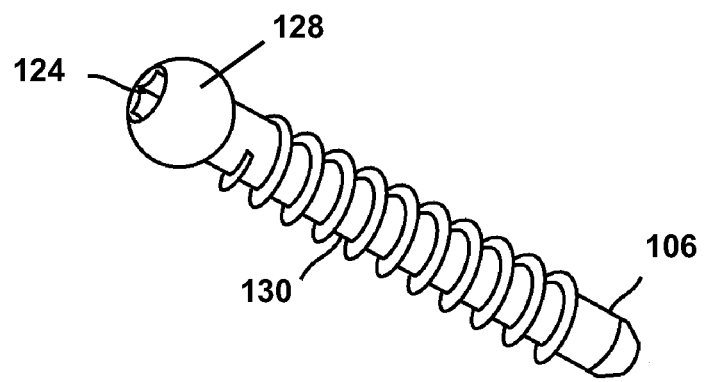
FIG. 6B is a perspective view of the expandable screw.

FIGS. 6a-6b illustrate one embodiment of the expanding screw 100 comprising an attachment point 190 for coupling a member 200 to the distal section 106 of the expanding screw 100. The member 200 may be any medical device or fixture that may be attached to the distal section 106 by way of a threaded engagement with the internal circumference of the shaft portion 130. In one embodiment, the head portion 120 includes a mating surface 128 for mating with a body member 225 (see FIGS. 7-8) forming a polyaxial pedicle screw. Alternatively, the head portion may mate with any type of screws, including monoaxial screws or any other screw assemblies, such as bone plates, fixation rods, and the like. Suitable screws that may be modified to include an attachment point 190 for attaching to the expanding screw 100 include those described in U.S. Publication No. 2008/0243189 and U.S. Pat. No. 7,377,923, the entirety of each of which is hereby incorporated by reference.

Figure 8:
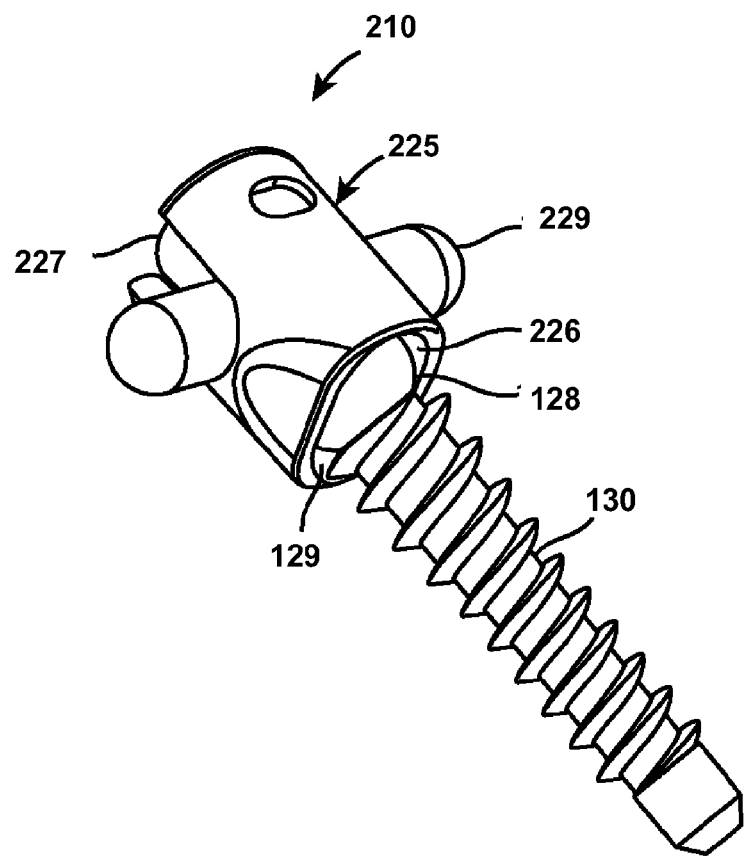
FIG. 8 is a perspective view of the variable angle spinal screw assembly.
Figure 9:
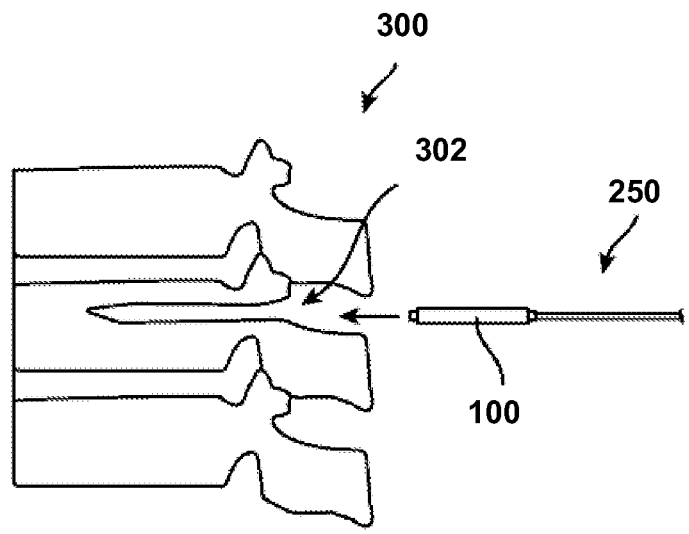
FIG. 9 is a side view illustrating a method for deploying the expandable screw into the treatment site in the vertebra.

With reference to FIGS. 8-9, a polyaxial pedicle screw comprises a body member 225 for receiving the head portion 128 of the expanding screw 100 which defines an opening 232 in an inner end thereof for the extension of the shaft portion 130 of the screw there through. The body member has a pair of opposed parallel slots for receiving a portion of a fixation rod there between. The body member also has a curvilinear interior surface disposed about the opening for abutting and mating with the substantially spherical head portion of the screw so as to allow variable angular movement of the body member with respect to the pedicle screw while maintaining the interior surface of the body member in mating contact with the head portion of the screw. The polyaxial screw further comprises a locking cap releasably securable within the body member such that the cap bears against the portion of a fixation rod disposed between the slots to secure the rod within the assembly. The polyaxial screw also comprises a keyed interface between the pedicle screw and the body member whereby the pedicle screw can be inserted into a vertebrae and the body member subsequently disposed about the substantially spherical head portion of the screw such that the head portion abuts and mates with the curvilinear interior surface of the body member to provide the variable angular movement of the body member with respect to the screw. The keyed interface comprises a first threaded surface in the body member about the opening in the inner end thereof and a second threaded surface on the head portion of the screw. The first threaded surface is adapted to threadably engage the second threaded surface such that the screw can be inserted into a vertebrae and the body member can be threaded onto and over the head portion of the screw to position the curvilinear interior surface of the body member such that the interior surface can abut and mate with the body portion.

In other embodiments, the shaft portion 130 can have a tapered shape with a screw thread 131 about the radial outside of shaft portion 130. In other embodiments, the shaft portion 130 can have a non-tapered shaped and/or no radial outside screw threads 131. In one particular embodiment, expanding screw 101 can have hollow shaft 130, neck 122 and head 120 portions along the inner longitudinal axis of the polyaxial screw in order to allow a guide wire (not shown) to be threaded through the polyaxial screw to help facilitate insertion of the screw during surgery. Additionally, the radial inside of polyaxial screw 100 at its distal end 106 can have screw threading (not shown) to allow it to fixedly and releasably attach to a medical device. It shall be understood that a variety of shaft designs are interchangeable with the present design. The specific choice of shaft features, such as thread pitch, shaft diameter to thread diameter ratio, overall shaft shape, etc. may be varied as needed.

The head portion 120 of the screw 100 can comprise a semi-spherical shape, which has a recess 124 in it (see FIGS. 6a-6b, discussed in further detail below). It is to be understood that the semi-spherical shape can be a section of a sphere, greater in extent than a hemisphere, and exhibiting an external contour which is equidistant from a center point of the head. In a preferred embodiment, the major cross-section of the semi-spherical head portion 120 includes at least 270 degrees of a circle.

Referring to FIG. 6b, the recess 124 of screw 100 defines a receiving locus for the application of a torque for driving the screw 100 into bone. The specific shape of the recess 124 may be chosen to cooperate with any suitable screw driving tool. For example, the recess 124 may comprise a slot for a flat-head screwdriver, a crossed recess for a Phillips head screwdriver, or most preferably, a hexagonally shaped hole for receiving an Allen wrench. It is further preferable that the recess 124 be co-axial with the general elongate axis of the screw 100, and most particularly with respect to the shaft portion 130. Having the axes of the recess 124 and the shaft portion 130 co-linear facilitates the step of inserting the screw 100 into bone in some embodiments.

Figure 7:
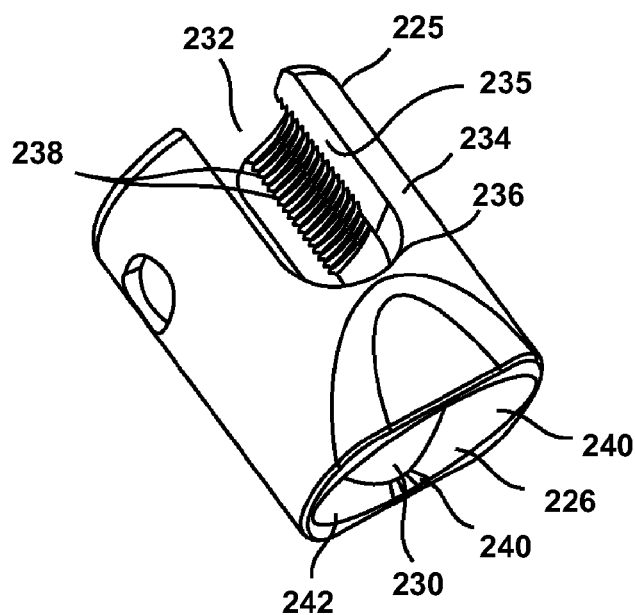
FIG. 7 is a perspective view of the body member.

FIGS. 7-8 show the spinal fixation device 210 including the screw 100, body member 225 and locking cap 227. The spinal fixation device 100 is used with at least one other such device and a stabilization or fixation rod 229 to connect the assemblies and stabilize the vertebras into which the assemblies are inserted. As discussed above, the screw 100 has a spherical head 120 defining slot 124 therein used to drive the screw into the bone. The rounded surface defined by the lower portion of screw head 120 rests upon and mates with a rounded interior surface 226 formed in the inner or lower end of the body member 225 so as to form a modified ball joint that provides the desired variable angular movement of the body member with respect to the embedded pedicle screw. The threaded shaft portion of screw 100 extends therefrom through the opening 230 in the lower end of body member 225.

The body member 225 further defines a pair of opposed parallel slots 232 axially disposed in the side wall 234 thereof, which terminate at their lower ends in curvilinear surfaces 236. The two slots 232 are sized to receive the fixation rod 229 therein as shown in the drawings with the walls 235 defining the slots preferably extending upwardly beyond the midpoint of the rod and can be inclined slightly to provide a slight holding force on the rod prior to securing the rod with the locking cap 227. Thus, during assembly, the surgeon exerts a slight downward force on the rod, snapping the rod into the transverse channel defined by the aligned slots 232.

The outer or upper interior surface of side walls 234 of the body member 225 both have radially projecting serrations formed therein defining a plurality of axially aligned ratchet teeth or threads 238 that mate with external threads on the locking cap 227. The exterior bottom surface of body member 225 has spaced outwardly extending concave surface 240 formed therein and a pair of perpendicularly disposed concave surfaces 242. Surfaces 240 and 242, together with mating surfaces 128 and 129 on the screw head 120 and body member 225 of the assembly, provide an extended range of motion of the body member 125 with respect to the screw 100. In one embodiment, the range of motion is about +/−30° in all directions (as measured from the longitudinal axis of the screw) and about +/−40° in the inferior-superior direction, the outwardly (as viewed from the screw head) concave surfaces provide the +/−40° range of motion, for a total motion range of 80°. This extended range of motion, as compared to the prior art, allows the surgeon additional freedom in locating the screws and eases the assembly process by reducing the requirement for a rod contouring.

Similar to previously discussed devices, the expandable screw 100 can be made from, for example, a single or multiple stainless steel alloys, nickel titanium alloys (e.g., Nitinol), surgical grade titanium alloy (for example, Ti-6Al-4V, ASTM F 136), commercially pure titanium (for example, Ti-CP2, ASTM F 67) with or without an electrolytic conversion coating, cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEB AX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA)s polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum, and gold.

The expandable screw 100 can be filled, coated, layered, and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

Figure 10:
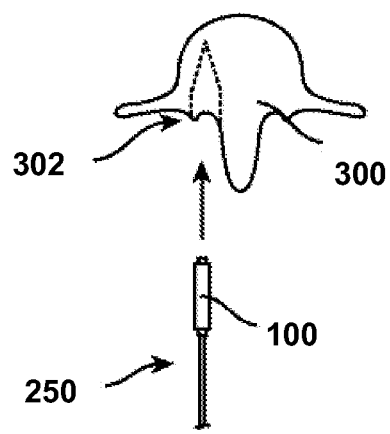
FIG. 10 is a top view illustrating a method for deploying the expandable screw into the treatment site in the vertebra.

FIGS. 9-10 illustrate that the expandable screw 100 can be coupled to the deployment tool 250 and inserted into a prepared hole within the spine. The deployment tool 250 can be deployed from the posterior side of the vertebral column 300. The deployment tool 250 can be deployed off-center, for example, when approaching the posterior side of the vertebral column 300. Once inserted, the expandable screw 100 can be deployed. The expandable screw 100 can be made from a shape memory alloy that can have a predetermined transition temperature such that expansion takes place due to temperature changes passively (e.g., from the patient's body heat) or actively (e.g., from thermal and/or electrical energy delivered to the screw 100 from outside the patient) created during or after implantation.

FIG. 11*a* shows the expandable screw normally attached to the posterior side of a vertebra through the pedicle of the vertebra using a polyaxial pedicle screw with a housing to connect the head of the screw to a rod of the spinal fixation system. FIG. 11*b* shows the expandable screw in the expandable position.

Referring now to FIGS. 1A, 1B, 11A, and 11B, the expandable screw 100 includes the shaft 130 having the longitudinal axis 101, an outer surface including a thread 132 to engage bone, and an expandable region near the middle portion 104 that is configurable between a first state shown in FIGS. 1A and 11A with a first radius R1 measured from the longitudinal axis 101 to the outer surface and a second state shown in FIGS. 1B and 11B having a second radius R2 measured from the longitudinal axis to the outer surface. The head 120 may be coupled with the shaft 130 at the neck 122 and configured to receive a driving instrument, such as with the recess 124 of FIG. 2, to insert and drive the shaft into the bone when the expandable region is in the first state. The cut pattern 134 on the shaft 130 permits at least partial nesting of a first portion of the expandable region within a second portion of the expandable region in the second state as best illustrated in FIG. 1C.

For example, the first portion may include a first threaded portion 133 that forces the second portion, which may include an adjacent second threaded portion 133, radially outward as the first portion nests within the second portion. The cut pattern 134 forms a first cut surface, such as top portion 135a, and a second cut surface, such as 135b, and the first cut surface substantially engages with the second cut surface in the first state as shown in FIG. 2. The first cut surface at least partially advanced along the longitudinal axis 101 past the second cut surface in the second state as shown in FIG. 1C. The cut surface 135a may be disposed opposite the cut surface 135b in the first state and engage a depth of the thread 131 in the second state. The cut surface 135a may be disposed opposite the cut surface 135b in the first state and opposite a portion of the thread 131 in the second state. The cut pattern 134 may include a spiral cut substantially parallel with a spiral path of the thread 131 along the length of the shaft 130.

The expandable region may include a hollow length of any portion of the shaft 130 and include a sidewall 150, a first section 150a of the sidewall at least partially overlapping a second section 150b of the side wall in the second state. The first section 150a may at least partially engage with the second section 150b in the second state. The expandable region may include a hollow length of the shaft 130 formed by a circumferential sidewall 150 and the cut pattern 134 traverses a thickness of the sidewall 130.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An expandable screw comprising:
a shaft having a longitudinal axis, the shaft having a proximal portion opposite a distal portion and an expandable region disposed between the proximal portion and distal portion, the shaft having an outer surface including a thread to engage bone, the expandable region configurable between a first state with a first radius measured from the longitudinal axis to the outer surface and a second state having a second radius measured from the longitudinal axis to the outer surface;
a head coupled with the shaft at a neck configured to receive a driving instrument to insert and drive the shaft into the bone when the expandable region is in the first state;
a center post extending distally from the head and coaxial with and internal to the shaft to provide support to the shaft, the center post having a central lumen configurable for a deployment rod to extend through the center post and couple with the distal portion of the shaft; and
a slit generally spiraling along the shaft and extending radially inwardly from the outer surface to the center post so as to define a cut pattern on the shaft that permits at least partial nesting of a first portion of the expandable region within a second portion of the expandable region in the second state.

2. The expandable screw of claim 1, wherein the first portion forces the second portion radially outward as the first portion nests within the second portion.

3. The expandable screw of claim 1, wherein the cut pattern forms a first cut surface and a second cut surface, the first cut surface substantially engaged with the second cut surface in the first state.

4. The expandable screw of claim 1, wherein the cut pattern forms a first cut surface and a second cut surface, the first cut surface at least partially advanced along the longitudinal axis past the second cut surface in the second state.

5. The expandable screw of claim 1, wherein the cut pattern forms a cut angle measured from the longitudinal axis and in a plane intersecting the longitudinal axis, the cut angle including a non-normal angle.

6. The expandable screw of claim 1, wherein the cut pattern forms a first cut surface on the first portion and a second cut surface on the second portion, wherein the second cut surface is disposed opposite the first cut surface in the first state and engages a depth of the a depth of a threaded portion on the first portion in the second state.

7. The expandable screw of claim 1, wherein the cut pattern forms a first cut surface on the first portion and a second cut surface on the second portion, wherein the second cut surface is disposed opposite the first cut surface in the first state and opposite a portion of the thread on the first portion in the second state.

8. The expandable screw of claim 1, wherein the cut pattern includes a spiral cut substantially parallel with a spiral path of the thread.

9. The expandable screw of claim 1, wherein the expandable region includes a hollow length of the shaft having a sidewall, a first section of the sidewall at least partially overlapping a second section of the side wall in the second state.

10. The expandable screw of claim 1, wherein the expandable region includes a hollow length of the shaft formed by a circumferential sidewall and the cut pattern traverses a thickness of the sidewall.

11. An expandable screw comprising:
a shaft having a longitudinal axis having a proximal portion, and a distal portion;
a center post extending distally from the proximal portion and coaxial with and internal to the shaft to provide support to the shaft, the center post having a central lumen configurable for a deployment rod to extend through the center post and couple with the distal portion of the shaft;

a thread winding along on an outer surface of the shaft; and a cut pattern defined by a slot disposed on the outer surface of the shaft and generally parallel to the thread so as to be generally spiraling along the shaft, whereby the cut pattern is configured to coaxially expand the shaft along at least a portion of the shaft to an expanded state, when the shaft is introduced into a bone, wherein the cut pattern closes in on itself at an angle such that adjacent threaded portions nest against each other to maintain a closed structure.

12. The expandable screw of claim 11, wherein the shaft includes at least one portion that expands coaxially greater than an adjacent portion in the expanded state.

13. The expandable screw of claim 12, wherein each threaded portion includes a top portion and a bottom portion, whereby the top portion of one threaded portion abuts against the bottom portion of an adjacent threaded portion in the expanded state.

14. The expandable screw of claim 13, wherein the top portion includes an angled inner surface that abuts with the bottom portion of an adjacent threaded portion, as to maintain the closed structure.

15. The expandable screw of claim 14, further comprising a head portion coupled to a neck portion disposed substantially within the proximal portion of the screw and the head portion coupled to a center post coaxially disposed within the shaft, whereby the application of force to the head portion coaxially expands the threaded portions of the shaft.

16. The expandable screw of claim 11, wherein the threaded portions include a first portion and a second portion with the cut pattern forming a first cut surface on the first portion and a second cut surface on the second portion, wherein the second cut surface is disposed opposite the first cut surface in the first state and engages a depth of the threaded portion on the first portion in the second state.

17. An expandable screw comprising:

a shaft having a longitudinal axis, the shaft having a proximal portion opposite a distal portion and an expandable region disposed between the proximal portion and distal portion, the shaft having an outer surface including a thread to engage bone, the expandable region configurable between a first state with a first radius measured from the longitudinal axis to the outer surface and a second state having a second radius measured from the longitudinal axis to the outer surface;

a head coupled with the shaft at a neck configured to receive a driving instrument to insert and drive the shaft into the bone when the expandable region is in the first state;

a center post extending distally from the head and coaxial with and internal to the shaft to provide support to the shaft; and a slit generally spiraling along the shaft and extending radially inwardly from the outer surface to the center post so as to define a cut pattern on the shaft that permits at least partial nesting of a first portion of the expandable region within a second portion of the expandable region in the second state, the cut pattern forming a first cut surface on the first portion and a second cut surface on the second portion, wherein the second cut surface is disposed opposite the first cut surface in the first state and engages a depth of the thread on the first portion in the second state.

18. The expandable screw of claim 17, wherein the first portion forces the second portion radially outward as the first portion nests within the second portion.

19. The expandable screw of claim 17, wherein the cut pattern forms a first cut surface and a second cut surface, the first cut surface substantially engaged with the second cut surface in the first state.

20. The expandable screw of claim 17, wherein the cut pattern forms a first cut surface and a second cut surface, the first cut surface at least partially advanced along the longitudinal axis past the second cut surface in the second state.

* * * * *